United States Patent
Cinquin (10) Patent No.: US 9,955,794 B2
(45) Date of Patent: May 1, 2018

(54) SUPPORT DEVICE FOR SUPPORTING A BODY, IN PARTICULAR A HUMAN BODY

(71) Applicant: System Assistance Medical, Ledat (FR)

(72) Inventor: Sébastien Cinquin, La Sauvetat-sur-Lede (FR)

(73) Assignee: System Assistance Medical, Ledat (FR)

( * ) Notice: Subject to any disclaimer, the term of this patent is extended or adjusted under 35 U.S.C. 154(b) by 352 days.

(21) Appl. No.: 14/759,147

(22) PCT Filed: Jan. 2, 2014

(86) PCT No.: PCT/EP2014/050002
§ 371 (c)(1),
(2) Date: Jul. 2, 2015

(87) PCT Pub. No.: WO2014/106624
PCT Pub. Date: Jul. 10, 2014

(65) Prior Publication Data
US 2015/0335167 A1  Nov. 26, 2015

(30) Foreign Application Priority Data
Jan. 4, 2013 (FR) ...................... 13 50044

(51) Int. Cl.
*A47C 27/10* (2006.01)
*A47C 27/08* (2006.01)
(Continued)

(52) U.S. Cl.
CPC ............ *A47C 27/10* (2013.01); *A47C 27/081* (2013.01); *A61B 5/1115* (2013.01);
(Continued)

(58) Field of Classification Search
CPC .... A47C 27/081; A47C 7/10; A61G 7/05792; A61G 7/05776; A61G 2203/34; A61G 2203/40
See application file for complete search history.

(56) References Cited

U.S. PATENT DOCUMENTS 5,560,374 A * 10/1996 Viard ................. A61G 7/05769
5/713
5,815,864 A * 10/1998 Sloop ................. A61G 7/05769
5/706
(Continued)

FOREIGN PATENT DOCUMENTS

WO     93/07949 A1    5/1993
WO  2008/138074 A1   11/2008

OTHER PUBLICATIONS

International Search Report dated Apr. 9, 2014, issued in corresponding International Application No. PCT/EP2014/050002, filed Jan. 2, 2014, 3 pages.

*Primary Examiner* — Eric J Kurilla
(74) *Attorney, Agent, or Firm* — Christensen O'Connor Johnson Kindness PLLC (57) ABSTRACT

Support device for supporting a body or a part of a body, in particular of a human body, comprising at least one deformable element with a first face and a second face opposite each other and provided with at least one detection means for detecting deformations of said deformable element, in which the detection means comprises: a substrate sheet (20), which is connected to one of the faces of said deformable element (6) extending parallel thereto and is provided with a plurality of metal windings (19) formed flat on at least one face of this substrate sheet, and a plurality of metal pellets (28), which are connected to the other face of said deformable element.

12 Claims, 8 Drawing Sheets

(51) Int. Cl.
*A61G 7/057* (2006.01)
*A61B 5/11* (2006.01)

(52) U.S. Cl.
CPC ..... *A61G 7/05776* (2013.01); *A61G 7/05792* (2016.11); *A61G 7/05715* (2013.01); *A61G 2203/34* (2013.01); *A61G 2203/36* (2013.01)

(56) References Cited

U.S. PATENT DOCUMENTS

| | | | |
|---|---|---|---|
| 6,009,580 | A | 1/2000 | Caminade |
| 6,943,694 | B1* | 9/2005 | Ellis .................... A47C 27/082 200/85 A |
| 7,378,975 | B1 | 5/2008 | Smith |
| 7,414,536 | B2* | 8/2008 | Call .................... A61G 5/1043 340/589 |
| 8,024,828 | B2* | 9/2011 | Nihei ................ A61G 7/05776 5/654 |
| 2002/0027384 | A1* | 3/2002 | Zur ...................... A61G 5/1043 297/452.41 |
| 2006/0085919 | A1* | 4/2006 | Kramer ................. A47C 7/022 5/713 |
| 2007/0285269 | A1* | 12/2007 | Geay .................. A61G 7/05769 340/686.1 |
| 2008/0005843 | A1* | 1/2008 | Lokhorst .............. A47C 27/082 5/655.3 |
| 2009/0056020 | A1* | 3/2009 | Caminade .............. A61B 5/447 5/600 |
| 2009/0100604 | A1* | 4/2009 | Caminade .......... A61G 7/05776 5/713 |
| 2009/0314354 | A1* | 12/2009 | Chaffee ................ G05D 16/208 137/14 |
| 2010/0308846 | A1* | 12/2010 | Camus ................... G01L 1/142 324/679 |
| 2011/0302719 | A1 | 12/2011 | Schwirian |
| 2012/0061943 | A1* | 3/2012 | Nihei ...................... A47C 4/54 280/304.1 |
| 2014/0059781 | A1* | 3/2014 | Lafleche .............. A47C 27/083 5/713 |

* cited by examiner

SUPPORT DEVICE FOR SUPPORTING A BODY, IN PARTICULAR A HUMAN BODY

The present invention relates to the field of support devices for supporting a body or a part of a body, in particular of a human body, which are intended for forming at least partially pads or mattresses and for being used in particular in the medical field for the comfort of the patients in a prone or seated position, particularly for the prevention of bed sores.

The patent EP 0 676 158 describes an air mattress which includes a plurality of inflatable vertical tubes and which is provided with deformation detection means which includes a metal sheet placed on the upper face of the mattress and a sheet provided with an inductive element such as an induction coil placed under the mattress, the metal sheet and the induction coil covering a zone that includes several inflatable tubes, as well as an electronic circuit connected to the inductive element for delivering an electrical signal corresponding to the distance between the metal sheet and the induction coil, which varies depending on the crushing of the mattress. Putting a means for inflation of the mattress under the control of said electrical signal can make it possible to set the distance between the metal sheet and the induction coil at a set value.

The patent WO 98/27850 describes an assembly which includes a mattress and below the mattress a deformation detection means which extends over a zone of the mattress and which includes a spacer element of variable thickness, a metal sheet between the mattress and this spacer element and an impedance variator element on the lower face of this spacer element. The deformations of the mattress under the effect of the load induce deformations of the spacer element which are measured by the impedance variations of the impedance variator element.

The patent WO 99/04673 describes a pad which is formed by a plurality of inflatable cells projecting upward with respect to a base sheet and which is provided with individual deformation sensors which are housed respectively inside of the cells. Each sensor includes a resiliently deformable element and a switch which is subject to this deformable element or else a reflective photoelectric sensor.

The document U.S. Pat. No. 6,009,580 describes a mattress composed of adjacent tubes extending over the whole width of the mattress. This mattress is provided with a sinkage detector which includes, over a central zone covering several adjacent tubes, an impedance variator element such as a self-induction coil situated under the mattress and a metal sheet situated on the mattress.

The known arrangements described above do not result in complete satisfaction. In particular, the detection of sinkage of the mattress is imprecise and not very reliable. The positioning, maintaining and replacement of the detection means are difficult and expensive. Furthermore, the known devices are not applicable for detecting the sinkage of just any supports.

The aim of the present invention is to propose an improvement for the support devices.

Proposed is a support device for supporting a body or a part of a body, in particular of a human body, which includes at least one deformable element having a first face and a second face on opposite sides and which is provided with a device for detection of deformations of said deformable element.

According to an embodiment, the deformable element includes a base sheet and at least a plurality of inflatable hollow cells projecting on one side of the base sheet and which are individually deformable in terms of height with respect to the base sheet, and the detection means includes a substrate sheet associated with said base sheet, extending parallel to it, and provided with a plurality of metal windings formed flat on at least one face of this substrate sheet, and a plurality of metal pellets associated respectively with the end parts of said inflatable hollow cells, away from said base sheet.

The deformation detection means can include a pulse induction detection means connected to said windings.

The deformation detection means can include a means making it possible to sequentially and successively connect the windings or groups of windings to said pulse induction detection means.

The windings can be divided into groups of windings in which the windings are electrically connected in series.

The metal pellets can be situated above the central parts of the metal windings.

The metal pellets can be borne by at least one flexible sheet extending above the end parts of said inflatable hollow cells.

The metal pellets can be attached on the end parts of said inflatable hollow cells.

The metal pellets can be attached on an interior face of the hollow cells, parallel to said base sheet.

The substrate sheet can be situated on the opposite side of the base sheet from said hollow cells.

The interior spaces can be connected by means of channels made in the base sheet.

The inflation element can include a first sheet and a second sheet which are adjoined forming said base sheet and plurality of hollow protuberances connected to said second sheet and delimiting said hollow cells, at least one of the sheets being configured so as to form communication channels between the interior spaces of the hollow cells.

The deformable element can include a resiliently deformable block, the metal pellets being borne by at least one flexible sheet.

Also proposed is an assembly which includes the inflatable support device, and which includes a pump and exhaust system connected to an exterior connection means which is connected to said hollow cells by channels included in the base sheet, and an electronic unit for pulse induction detection connected to exterior electrical connection means which are connected to said windings and for management of the activation of the pump and exhaust system.

Also proposed is an assembly which includes a support device and which includes an electronic unit for pulse induction detection connected to exterior electrical connection means which are connected to said windings and for management of an alarm.

Support devices and its accessories will now be described as non-limiting examples illustrated by the drawing in which.

Figure 1:
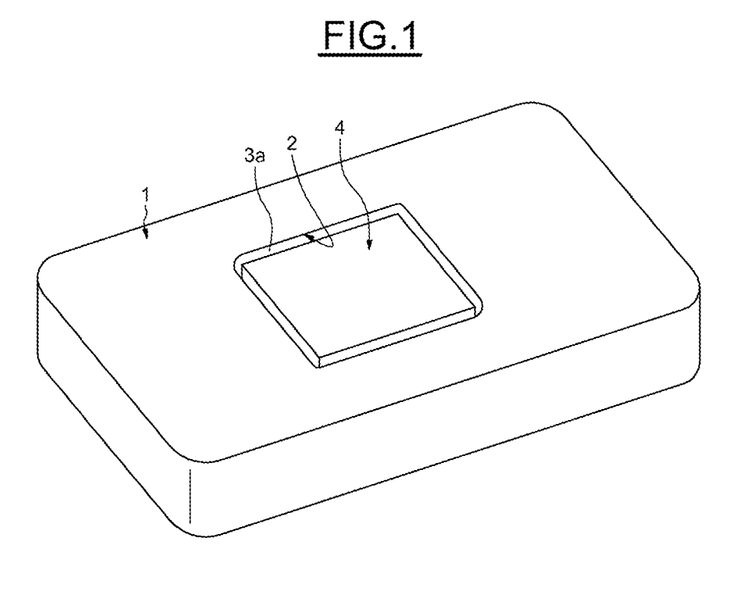
FIG. 1 represents in perspective a bedding mattress provided with a support device provided with a deformation detection means.
Figure 2:
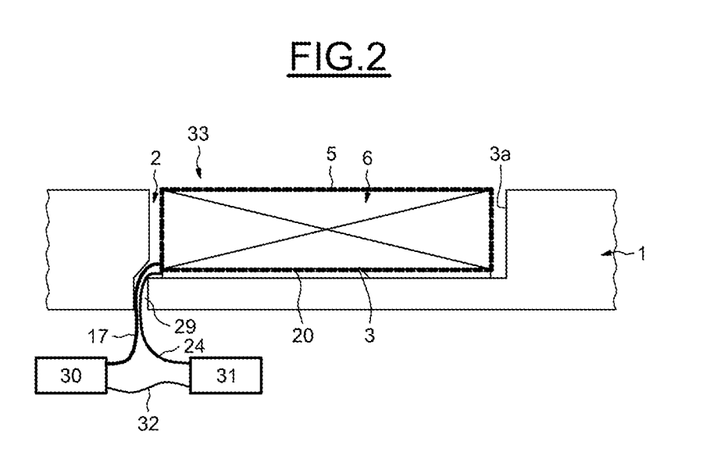
FIG. 2 represents a diagrammatic partial vertical section of the bedding mattress provided with a support device of FIG. 1 and means for managing the latter.

As illustrated in FIGS. 1 and 2, a bedding mattress 1 has a recess 2 open towards the top and which has a bottom 3, for example, rectangular or square, and a peripheral wall 3a. For example, the recess 2 is produced in a central part of the mattress 1 in a zone going from the middle of the thigh to the middle of the back of a user lying on the mattress 1.

Installed inside of this recess 2 is a support device 4 which occupies substantially the whole volume of the recess 2 and whose upper face is substantially in the plane of the upper face of the mattress 1.

The support device 4 includes, for example, wrapped in a flexible cover 5, an inflatable deformable element 6 of general paralellepipedic shape.

Figure 3:
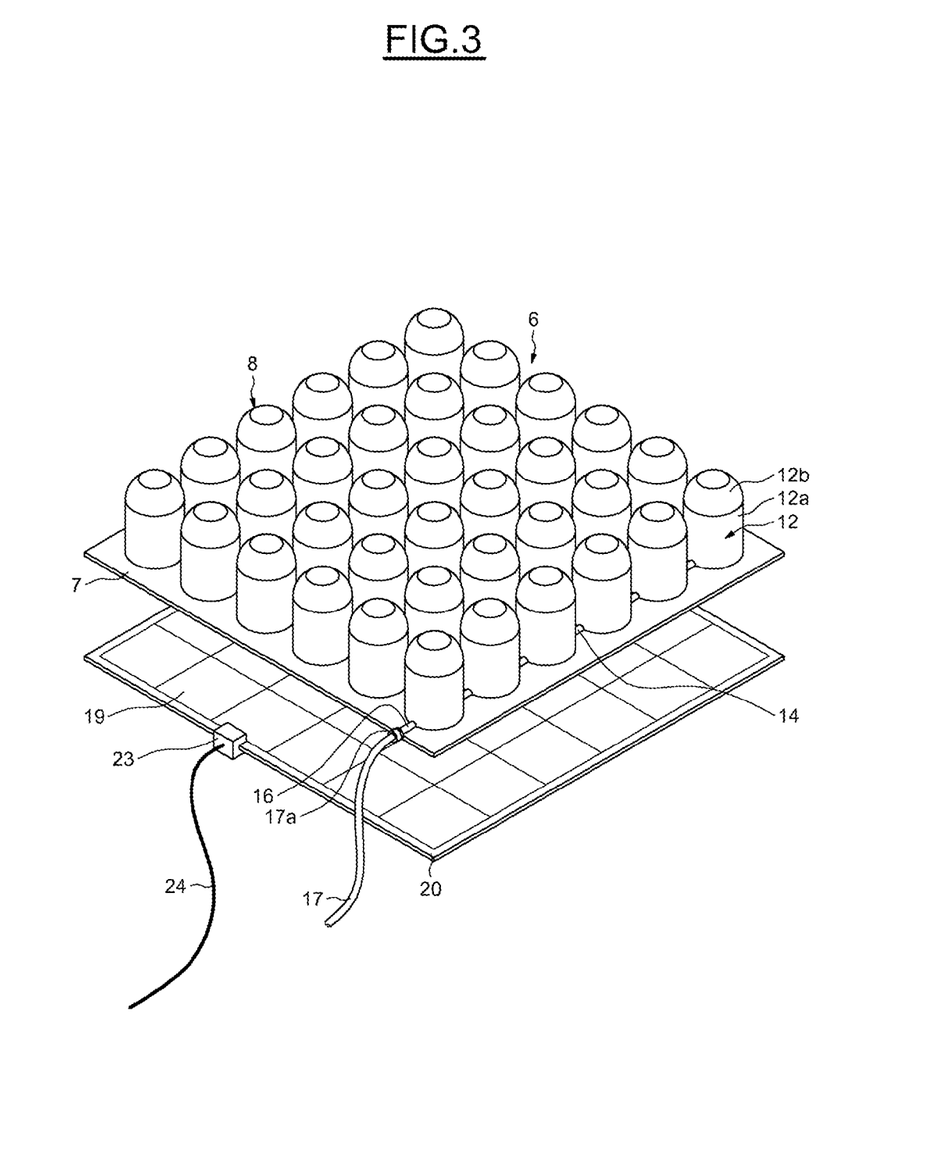
FIG. 3 represents an exploded perspective view of the support device and of an associated substrate sheet.
Figure 4:
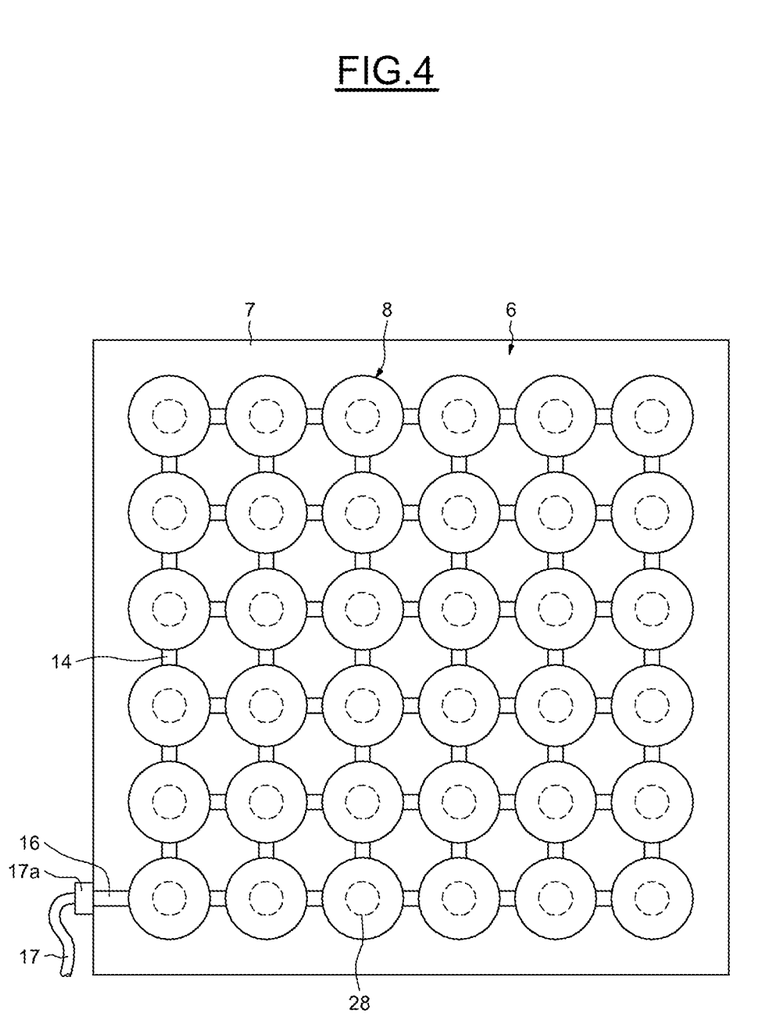
FIG. 4 represents a top view of the support device.
Figure 5:
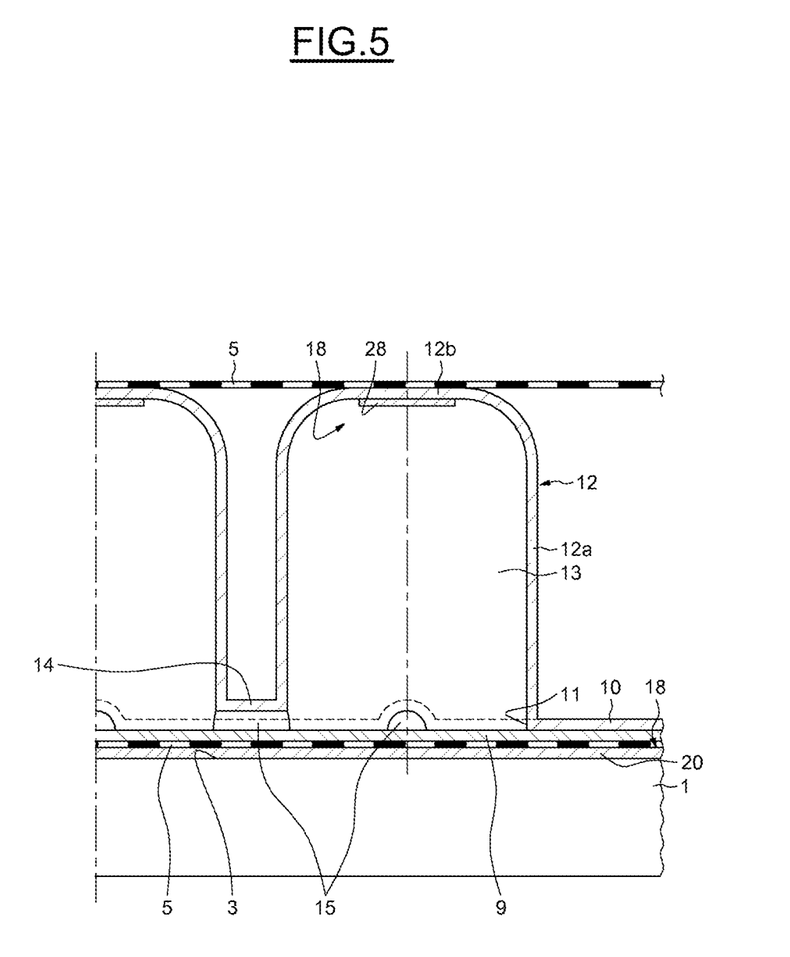
FIG. 5 represents a detailed partial vertical section of the bedding mattress provided with the support device of FIGS. 3 and 4.

As illustrated in FIGS. 3 to 5, the inflatable element 6, for example, made of a flexible plastic or rubber material, includes a base sheet 7 adjacent and parallel to the bottom 3 of the recess 2 of the mattress 1 and a plurality of inflatable hollow cells 8 projecting upward on one side of the base sheet 7, which are distributed in the widthwise direction and in the lengthwise direction of the mattress and which are individually deformable in particular in terms of height with respect to the base sheet 7.

For example, the base sheet 7 covers substantially the whole bottom 3 of the recess 2 of the mattress 1 and is substantially rectangular. The hollow cells 8, substantially cylindrical, are, for example, distributed substantially over the whole surface of the base sheet 7 in a square matrix and are situated a short distance from one another. According to an embodiment variant, the hollow cells 8 could be distributed in a diamond-shaped matrix. According to the example represented, thirty-six cells are provided, arranged in six columns and six lines that are orthogonal.

As illustrated more particularly in FIG. 5, the inflatable element 6 is made up of a first part formed by a first sheet 9, and of a second part formed, in a single piece, by a second sheet 10 having a plurality of openings 11, and by a plurality of hollow protuberances 12 projecting upward from the edges of the openings 11. The first sheet 9 and the second sheet 10 are adjoined and attached together by adhesive and form the base sheet 7. The hollow protuberances 12 and the corresponding parts of the first sheet 9 delimit the interior spaces 13 of the hollow cells 8.

The hollow protuberances 12 have a peripheral wall 12a of circular or star-shaped section and an upper end wall 12b with a flat central part.

The second sheet 10 has a plurality of small upward deformations 14 which, with the corresponding parts of the first sheet 9, delimit communication channels 15 connecting the interior spaces 13 of the adjacent hollow cells 8. Furthermore (FIGS. 3 and 4), the second sheet 10 has a small upward deformation 16 which, with a corresponding part of the first sheet 9, delimits a communication channel one of whose ends opens into a hollow cell and whose other end arranged on an edge of the base sheet 7 can be connected to a connection pipe 17 by means of a sealed connection means 17a.

The support device 4 is provided with a means 18 for detection of the deformations of the hollow cells 8 in the direction of their height.

Figure 6:
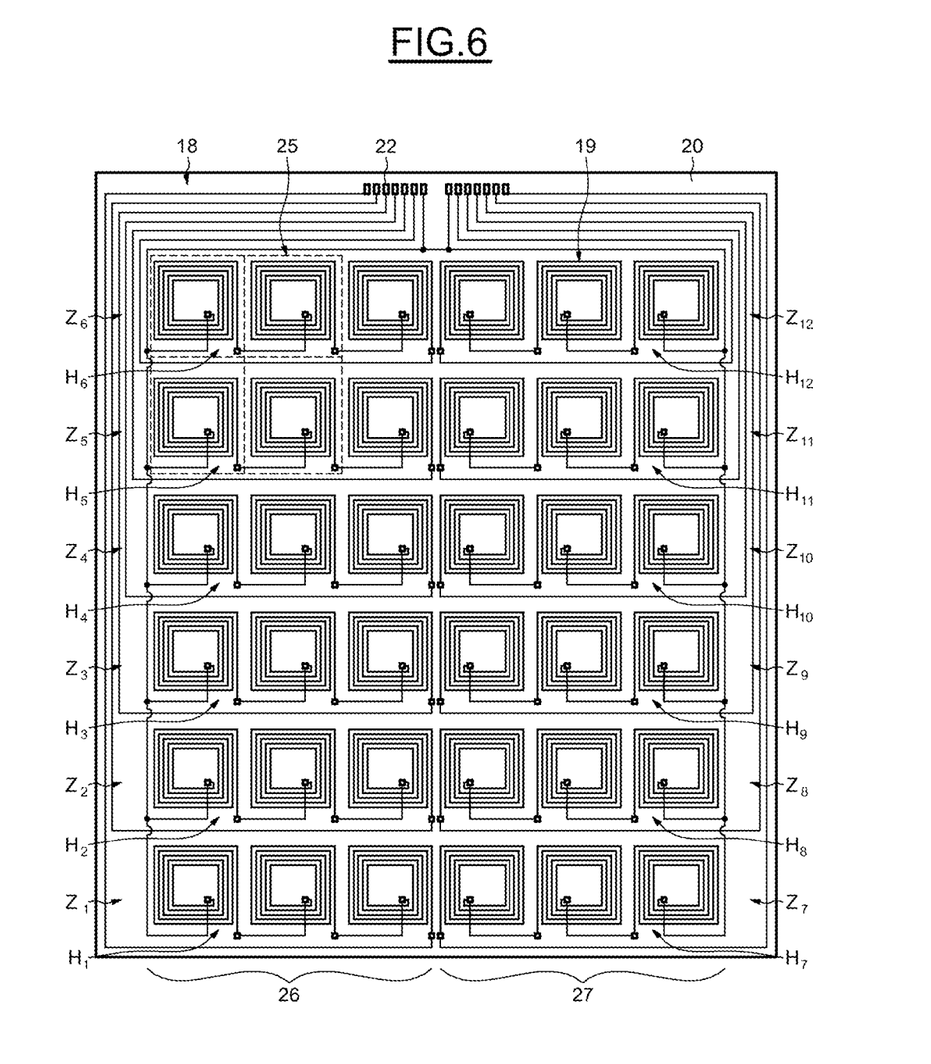
FIG. 6 represents a detailed front view of the substrate sheet of FIG. 3.

As illustrated in FIGS. 3 and 6, the detection means 18 includes a plurality of metal windings 19 screen printed flat on zones of a face of a substrate sheet 20, which is preferably made of a flexible plastic material.

As illustrated in particular in FIGS. 2 and 5, the substrate sheet 20 is associated with a face of the inflatable element 6 and more precisely is inserted between the base sheet 7 of the inflatable element 6 and the bottom 3 of the recess 2 of the mattress 1 and parallel to this base sheet 7. For example, the periphery of the substrate sheet 20 coincides with that of the base sheet 7.

As illustrated in FIGS. 3 and 6, the metal windings 19 are connected selectively, by electrical connection tracks 21, to exterior electrical connection contacts 22 arranged near one another and near an edge of the substrate sheet 20, the electrical connection tracks 21 and the electrical connection contacts 22 being screen printed on at least one face of the substrate sheet 20.

On the electrical connection contacts 22, an end connector 23 of an electrical connection cable 24 can be coupled.

According to the particular embodiment example illustrated in FIG. 6, the metal windings 19 are formed on adjacent zones 25 of the substrate sheet 20 and are distributed in a square matrix. According to an embodiment variant, the metal windings 19 could be distributed in a diamond-shaped matrix. Provided according to the example represented are thirty-six zones 25 arranged in six columns and six orthogonal lines.

The total surface area covered by the hollow cells 8 can substantially coincide with the total surface area covered by the metal windings 19, without this being necessarily obligatory. The number of hollow cells 8 can be equal to the number of metal windings 19, without this being necessarily obligatory.

On each line of said matrix of adjacent zones 25, the six metal windings 19 are divided into two groups 26 and 27 of three metal windings which are connected in series and connected to corresponding electrical connection contacts 22. Moreover, in each of these groups, the metal windings 19 are wound in the same direction, and from one group to the other, the metal windings 19 are wound in the opposite direction. Furthermore, the six groups 26 and the six groups 27, which are adjacent in the direction of the columns of said matrix, are wound in the same direction. Thus, the groups of windings 26 and 27 determine twelve detection zones $Z_1$ to $Z_{12}$ distributed over the surface of the substrate sheet 20, including six detection zones $Z_1$ to $Z_6$ in one column and six detection zones $Z_7$ to $Z_{12}$, which are provided respectively with inductive elements $H_1$ to $H_{12}$ each composed of three windings 19 connected in series.

As illustrated in FIG. 5, the detection means 18 moreover includes a plurality of metal pellets 28, in one or more parts, which are associated with another face of the inflatable element and which more precisely are attached on the end parts of the hollow cells 8, away from said base sheet 7 and a distance from the metal windings 19 borne by the substrate sheet 20. For example, the metal pellets 28 are inside of the hollow cells 8 and are glued respectively on the interior face of the flat central parts of the upper end walls 12b of the hollow protuberances 12, so that they are protected from any exterior aggression. In this case, the metal pellets 28 are positioned before gluing of the sheets 9 and 10 forming the base sheet 7.

In the case of the embodiment variant described in the preceding, the metal pellets 28 can be placed above the central parts of the windings 19, although this is not obligatory.

As illustrated in FIG. 2, the mattress 1 has a through-passage 29 opening into the recess 2 and open under the mattress. The connection pipe 17 and the electrical connection cable 24 extend through the passage 29.

The connection pipe 17 is connected to a pump and exhaust system 30, and the electrical connection cable 24 is connected to an electronic unit 31, the pump and exhaust system 30 and the electrical connection cable 24 being connected by an electrical cable 32. Thus, the support device 4, the substrate sheet 20 provided with the metal windings 19, the pump and exhaust system 30 and the electronic unit 31 constitute a functional assembly 33.

This functional assembly 33 can operate in the following manner.

The inflatable element 6 rests on the substrate sheet 3 by means of its base sheet 7, and the substrate sheet 3 rests on the bottom 3 of the recess 2 of the mattress 1.

When the body of a user exerts a load on the upper end parts of at least some of the hollow cells 8, the hollow cells 8 which are acted upon are respectively sunken in as a function of the local support pressures resulting from the internal pressure produced in the interior spaces 13 of the hollow cells 8 by the pump and exhaust system 30.

With the metal pellets 28 following the movements of the end parts of the hollow cells 8 to which they are firmly connected, the measurement or determination of the value of one or more electrical signals, which are representative of the electromagnetic coupling between the metal pellets 28 and the metal windings 19 supplied with electrical energy in a suitable manner by the electronic unit 31, constitutes a means evidencing the effects of the load on the hollow cells 8 or the degree of deformation of the latter.

By varying the pressure inside of the hollow cells 8, by setting or adjusting the pump and exhaust system 30, it is possible to vary the level of deformation or sinkage of the hollow cells 8 and the local pressures of the hollow cells 8 exerted on the body of the user.

According to a particular embodiment example, the electronic unit 31 is programmed so as to perform a pulse induction detection of the position of the metal pellets 25 with respect to the metal windings 19, and more particularly with respect respectively to the windings 19 included in the detection zones $Z_1$ to $Z_{12}$.

As is known in the field of electronics, a pulse induction detection occurs in the following manner. A winding constituting an inductive element or a self-induction coil is run through by a high current for a brief instant corresponding to the duration of a supply voltage pulse. Following this voltage pulse, an overvoltage is generated by induction at the terminals of the winding, this overvoltage decreasing very rapidly to the nominal value of the supply voltage. When a metal object is brought close to the winding, the duration of the return to this nominal value is increased, and all the more so the closer the object is to the winding. As a consequence, measuring or determining this return duration or the duration of the resultant voltage pulse including the supply voltage pulse and the return duration enables one to measure or determine the distance between the winding and the object.

Figure 7:
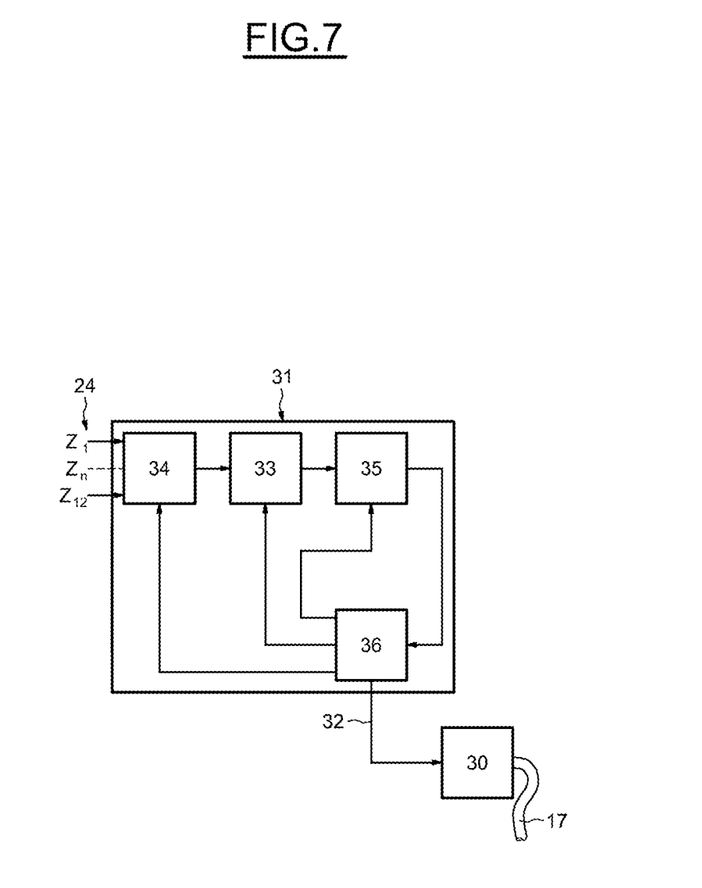
FIG. 7 represents an electronic diagram of a management system of the support device.

As illustrated diagrammatically in FIG. 7, the electronic unit 31, in order to apply the above, can include in particular:

a circuit 33 for measuring said return duration or said duration of the resultant voltage pulse, a demultiplexing circuit 34 for selectively connecting each of the inductive elements to the measurement circuit, a comparison circuit 35 for comparing said return duration or the duration of the resultant voltage pulse with a threshold REF1, which for example is settable, whose value corresponds to a predetermined return duration or a predetermined duration of said resultant voltage pulse, and a programmed logic circuit 36, or microprocessor, for controlling, according to measurement cycles, said circuits 33, 34 and 35 so as to successively obtain the results of the comparisons corresponding to the inductive elements $H_1$ to $H_{12}$ and to manage the operation of the pump and exhaust system 30 as a function of the results of the comparisons.

Considering the example of the aforementioned arrangement of the metal pellets 28 with respect to the metal windings 19, each metal pellet 28 can approximately be considered to influence the winding 19 situated below.

For each inductive element $H_1$ to $H_{12}$, the return duration or the duration of said resultant voltage pulse provides information with regard to the distance between the metal pellets 28 situated above the inductive element in consideration. This predetermined distance in fact integrates, for each inductive element, relative distances of one, two or three metal pellets 28 with respect to the metal windings 19 of which the inductive element is composed.

The comparison of the return duration or the duration of said resultant voltage pulse with the threshold REF1 provides information with regard to the position of the metal pellets 28 situated above the inductive element in consideration with respect to the substrate sheet 20. This comparison makes it possible to determine whether the sinkages or deformations of one, two or three hollow cells 8 are above or below a predetermined distance associated with the threshold REF1, with respect to the inductive element in consideration which is composed of the corresponding windings 19.

In order to take into account said comparison, the logic circuit 36 can be programmed to control the pump and exhaust system 30 so as to re-inflate the inflatable element 8 if the threshold REF is exceeded in the direction of deflation of said inflatable element.

A second threshold REF2 can also be set, and the logic circuit 36 can be programmed to control the pump and exhaust system 30 so as to deflate the inflatable element 8 if this second threshold REF2 is exceeded in the direction of inflation of said inflatable element.

The logic circuit 36 can be programmed to control the pump and exhaust system 30 so as to maintain the state of inflation of the inflatable element 8 so as to maintain the aforementioned distance in two extreme values corresponding to the first threshold REF1 and to the second threshold REF2.

According to an embodiment variant, the inflatable element 8 could be subdivided into at least two independent inflatable parts, possibly selectively managed by the pump and exhaust system 30 and the logic circuit 31 or managed otherwise.

According to another embodiment variant, the mattress 1 could include other support devices 6 placed at other suitable sites, possibly selectively managed by the pump and exhaust system 30 and the logic circuit 31 or managed otherwise.

According to another embodiment variant, the support device 6 could be integrated in another object such as the seat or back of a chair.

According to another embodiment variant, the support device 6 and the substrate sheet 20 provided with the metal windings 19 could form an independent pad associated with a pump and exhaust system 30 and an electronic unit 31 in order to constitute an independent functional assembly.

According to another embodiment variant, the electronic unit 31 could be provided with a sound or light alarm and could be programmed so as to activate this alarm, for example, when the sinkage of at least some hollow cells 8 exceeds a predetermined value, that is to say when the distance of at least some metal pellets 28 with respect to the metal windings 19 goes below a predetermined value.

Figure 8:
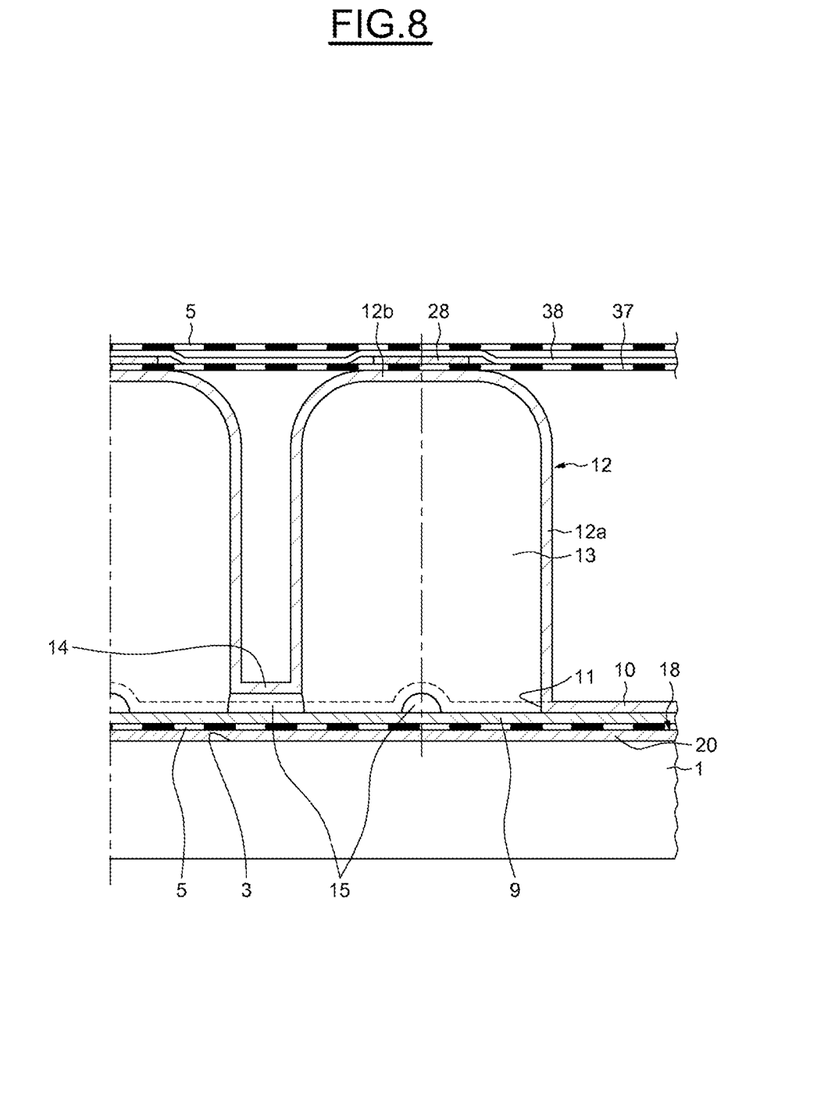
FIG. 8 represents an embodiment variant in section corresponding to that of FIG. 5.

According to another embodiment variant illustrated in FIG. 8, the metal pellets 28 are no longer borne by the ends of the inflatable cells 12 but are borne flat by a flexible sheet 37 extending over the ends of the cells 12, the metal pellets 28 being arranged over the flat central parts of the upper end walls 12*b* of the cells 8. For example, the metal pellets 28 can be inserted between the flexible sheet 37 and another sheet 38, these sheets being connected together.

Figure 9:
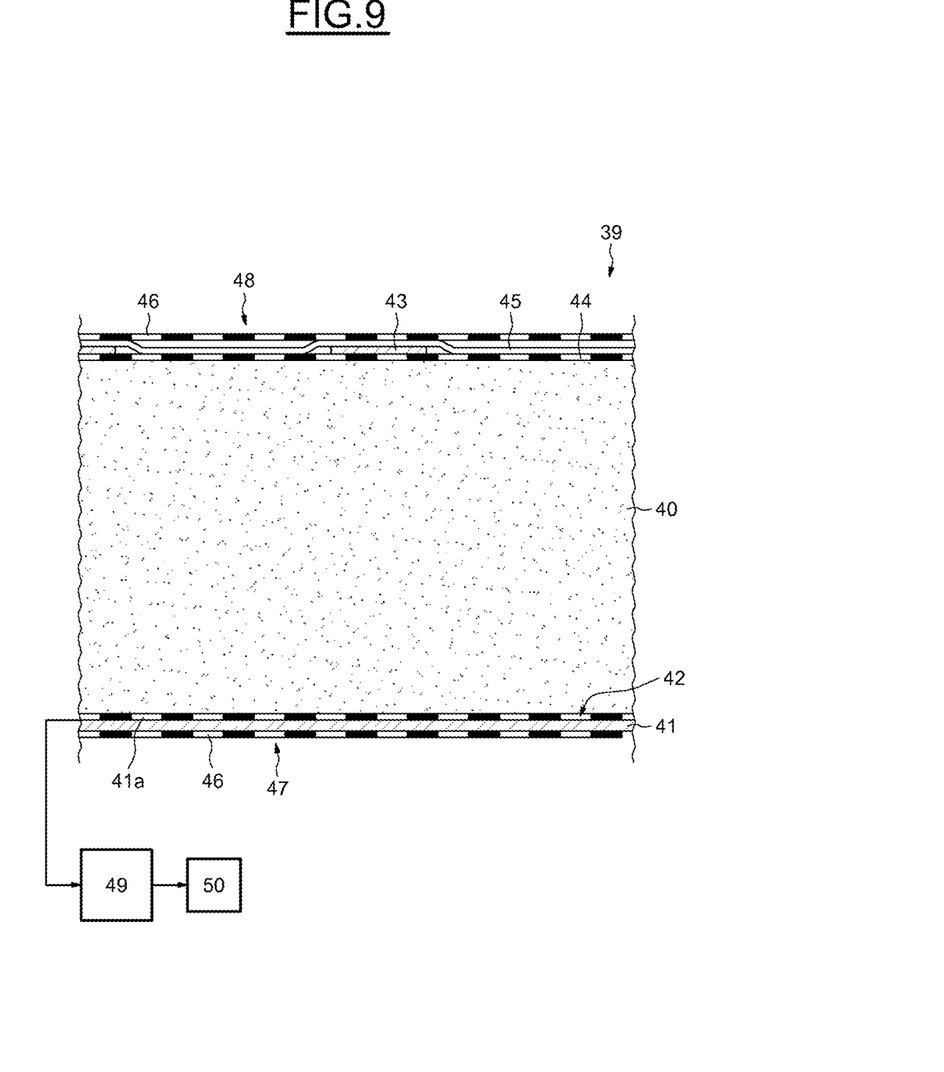
FIG. 9 represents another support device provided with another deformation detection means.

As illustrated in FIG. 9, another support device 39 includes a deformable element formed by a resiliently deformable block 40, for example, made of an expanded plastic foam, having opposite faces.

The resiliently deformable block 40 is provided with a substrate sheet 41 associated with and placed over one face of this block 40, with interposition of a protective sheet 41*a*. This substrate sheet 41 is equivalent to the substrate sheet 20 of the preceding example and, like this substrate sheet 20, is provided with a plurality of metal windings 42 lying flat and distributed.

The resiliently deformable block 40 is also provided with a plurality of distributed metal pellets 43 associated with the other face of the block 40 and arranged flat, these metal pellets 43 being equivalent to the metal pellets 28 of the preceding example.

Equivalently to the example of FIG. 8, the metal pellets 43 are, for example, inserted between two flexible sheets 44 and 45 which are connected together.

The above assembly can be inserted into an exterior cover 46.

The support device 39 thus constituted can form a pad or a mattress or a part of a pad or mattress and have a bearing face 47 on the side of the substrate sheet 41 that can be placed resting on an exterior support, and a face 48 on the side of the metal pellets 43 on which a person can come to rest.

Equivalently to the preceding example, the metal windings 42 borne by the substrate sheet 41 are connected to an electronic unit 49 which, equivalently to the electronic unit 31, is capable of detecting the sinkage of the resiliently deformable block 40 by detection that at least some metal pellets 43 are moving closer to the metal windings 42. The electronic unit 49 can be programmed to activate and a sound or light alarm 50 in the case in which this moving closer reaches a threshold.

Such an arrangement can be used for the purpose of indicating whether the support device 39 is poorly suited to the person using it.

According to an embodiment variant, the wrappings and the flexible sheets mentioned above can, for example, be made of resilient or extensible fabric.

The support devices and the deformation detection means just described have the advantages of achieving more homogeneous and reproducible detections, of having little or no sensitivity to possible exterior electromagnetic disturbances, of being simple to produce and of being easily protectable from exterior physical aggressions.

The present invention is not limited to the examples described above. Many other embodiment variants are possible, without leaving the scope of the invention.

The invention claimed is:

1. Support device for supporting a body or a part of a body, in particular of a human body, comprising:
at least one deformable element having a first face and a second face on opposite sides, a base sheet, and at least a plurality of inflatable hollow cells projecting on one side of the base sheet which are individually deformable in terms of height with respect to the base sheet; and
a device for detection of deformations associated with the deformable element, the device for detection of deformations comprising:
a substrate sheet associated with said base sheet, extending parallel to the base sheet, and provided with a plurality of metal windings formed flat on at least one face of the substrate sheet; and
a plurality of metal pellets coupled to end parts of said inflatable hollow cells away from said base sheet such that the metal pellets follow the movements of the end parts, wherein the metal pellets are situated above a central portion of the metal windings.

2. Device according to claim 1, wherein the device for detection of deformations includes a pulse induction connected to said windings.

3. Device according to claim 2, wherein the windings are divided into groups of windings in which the windings are electrically connected in series.

4. Device according to claim 3, wherein the device for detection of deformations is configured to sequentially and successively connect the windings or groups of windings to said pulse induction detector.

5. Device according to claim 1, wherein the metal pellets are borne by at least one flexible sheet extending above the end parts of said inflatable hollow cells.

6. Device according to claim 5, wherein interior spaces of the inflatable hollow cells are connected via communication channels made in the base sheet.

7. Device according to claim 6, wherein the deformable element includes a first sheet and a second sheet which are adjoined forming said base sheet and a plurality of hollow protuberances connected to said second sheet and delimiting said inflatable hollow cells, at least one of the first and second sheets being configured so as to form the communication channels between interior spaces of the inflatable hollow cells.

8. Device according to claim 1, in which wherein the metal pellets are attached on an interior face of the inflatable hollow cells parallel to said base sheet.

9. Device according to claim 1, wherein the substrate sheet is situated on the opposite side of the base sheet from said inflatable hollow cells.

10. Device according to claim 1, wherein the deformable element includes a resiliently deformable block, and wherein the metal pellets are borne by at least one flexible sheet.

11. Assembly which includes a support device according to claim 1, comprising:
a pump and exhaust system connected to an exterior connector which is connected to said hollow cells by communication channels included in the base sheet; and
an electronic unit for pulse induction detection connected to an exterior electrical connector which is connected to said windings and configured for management of the activation of the pump and exhaust system.

12. Assembly which includes a support device according to claim 1, comprising an electronic unit for pulse induction detection, the electronic unit connected to an exterior electrical connector which is connected to said windings and configured for management of an alarm.

* * * * *

UNITED STATES PATENT AND TRADEMARK OFFICE
CERTIFICATE OF CORRECTION

Page 1 of 1

PATENT NO. : 9,955,794 B2
APPLICATION NO. : 14/759147
DATED : May 1, 2018
INVENTOR(S) : S. Cinquin It is certified that error appears in the above-identified patent and that said Letters Patent is hereby corrected as shown below:

| Column | Line | Error |
|---|---|---|
| 8 (Claim 2, Lines 2-3) | 27-28 | "pulse induction connected" should read --pulse induction detector connected-- |

Signed and Sealed this
Seventh Day of August, 2018

Andrei Iancu
*Director of the United States Patent and Trademark Office*